US010786325B1

(12) United States Patent
Osa

(10) Patent No.: US 10,786,325 B1
(45) Date of Patent: Sep. 29, 2020

(54) ANCHOR BOLT FIXATION SYSTEM

(71) Applicant: PMT Corporation, Chanhassen, MN (US)

(72) Inventor: Benjamin Osa, Minneapolis, MN (US)

(73) Assignee: PMT Corporation, Chanhassen, MN (US)

( * ) Notice: Subject to any disclaimer, the term of this patent is extended or adjusted under 35 U.S.C. 154(b) by 203 days.

(21) Appl. No.: 15/842,166

(22) Filed: Dec. 14, 2017

Related U.S. Application Data

(60) Provisional application No. 62/434,706, filed on Dec. 15, 2016.

(51) Int. Cl.
| | |
|---|---|
| *A61B 17/00* | (2006.01) |
| *A61M 39/02* | (2006.01) |
| *A61B 17/34* | (2006.01) |
| *A61B 90/10* | (2016.01) |

(52) U.S. Cl.
CPC .... *A61B 90/10* (2016.02); *A61B 2017/00477* (2013.01); *A61B 2017/347* (2013.01); *A61B 2090/103* (2016.02); *A61M 2039/025* (2013.01); *A61M 2039/0279* (2013.01)

(58) Field of Classification Search
CPC ... A61B 2017/347; A61B 90/10; A61B 90/11; A61B 90/14; A61B 2090/101; A61B 2090/103; A61B 2039/025; A61B 2017/3407; A61B 2017/3419; A61B 2017/3482; A61B 2017/349; A61B 2017/3492; A61M 2039/0261; A61M 2025/025; A61N 1/0539

USPC .......................................................... 606/130
See application file for complete search history.

(56) References Cited

U.S. PATENT DOCUMENTS

| | | | |
|---|---|---|---|
| 5,121,949 A * | 6/1992 | Reese | ..................... F16L 47/04 285/255 |
| 5,843,150 A | 12/1998 | Dreessen et al. | |
| 5,865,842 A | 2/1999 | Knuth et al. | |
| 7,322,954 B2 | 1/2008 | Putz | |
| 7,787,934 B2 | 8/2010 | Mazzocchi et al. | |
| 8,603,038 B2 | 12/2013 | Nelson | |
| 8,915,846 B2 | 12/2014 | Miles et al. | |
| 2003/0195602 A1 * | 10/2003 | Boling | ...................... A61N 1/05 607/122 |
| 2008/0103456 A1 | 5/2008 | Johnson et al. | |
| 2012/0083739 A1 * | 4/2012 | Nelson | ............... A61B 17/3403 604/164.01 |
| 2013/0103048 A1 * | 4/2013 | Burg | ...................... A61B 90/11 606/129 |
| 2014/0206941 A1 * | 7/2014 | Stiner | ................ A61B 17/3417 600/205 |
| 2015/0031982 A1 * | 1/2015 | Piferi | ................... A61N 1/0534 600/411 |

* cited by examiner

*Primary Examiner* — Martin T Ton
(74) *Attorney, Agent, or Firm* — Eggink & Eggink; Anthony G. Eggink; Katrina M. Eggink

(57) ABSTRACT

An anchor bolt fixation system for catheter probes and electrodes having different diameters. A removable reducing tube is provided for insertion into the lumen of an anchor bolt and an anchor bolt cap is provided for securing the reducing tube to the anchor bolt. A second anchor bolt cap is provided having a bore with a diameter generally equal the diameter of the lumen of the reducing tube.

15 Claims, 4 Drawing Sheets

ANCHOR BOLT FIXATION SYSTEM

This application claims the benefit of U.S. Provisional Patent Application 62/434,706 filed on Dec. 15, 2016 and is fully incorporated by reference herein.

The present invention relates generally to an anchor bolt fixation system. Particularly the present invention relates to an anchor bolt fixation system constructed to be utilized with catheter probes and electrodes having different diameters.

BACKGROUND OF THE INVENTION

Anchor bolts are commonly utilized in burr holes in the skull of a patient for subsequent catheter and/or neurosurgical related electrode placements, for example. An anchor bolt may have an internal lumen of a specified diameter to permit access inside a patient's skull, for example. A neurosurgical procedure may require the use of catheters and/or electrodes of different diameters, thereby requiring the utilization of multiple anchor bolts to accommodate the required diameters. Neurological procedures, for example, may require the use of depth electrodes to record signals in locating the source of epileptic seizures (i.e. in stereoelectroencephalography methods (sEEG)). Other procedures may require the utilization of a laser probe for ablation of lesions in an MRI guided neurological procedure. The latter electrodes and probes require different diameter anchor bolt lumen. Therefore, a need exists for anchor bolt systems capable of using multiple diameter catheter probes and/or depth electrodes, for example.

The anchor bolt fixation system of the present invention provides for the use of multiple diameter probes and electrodes utilizing a single burr hole/anchor bolt in the skull and overcomes the difficulties and shortcomings of the prior art.

SUMMARY OF THE INVENTION

An anchor bolt fixation system utilizing an anchor bolt to accommodate the use of different diameter catheters and electrodes, for example. A removable diameter reducing tube is provided for insertion into the lumen of the anchor bolt. An anchor bolt cap is provided for securing the reducing tube to the anchor bolt body. A second anchor bolt cap is provided having a bore with a diameter generally equal to the diameter of the lumen of the reducing tube.

The anchor bolt fixation system of the invention provides a user to selectively utilize the lumen of the anchor bolt and/or the lumen of the reducing tube subsequent insertion of the diameter reducing tube into the lumen of the anchor bolt.

The advantages provided by the anchor bolt fixation system of the invention include utilizing a single targeted burr hole and associated anchor bolt in the skull for use by multiple diameter catheters and electrodes. The advantage provides a physician to more efficiently utilize the same targeted anchor bolt for different neurological purposes, for example.

These and other advantages of this invention will become clear from the following description by reference to the drawings.

DESCRIPTION OF THE PREFERRED EMBODIMENTS

The anchor bolt fixation system of the present invention provides for the use of multiple diameters of catheter probes and/or depth electrodes, for example.

Figure 1:
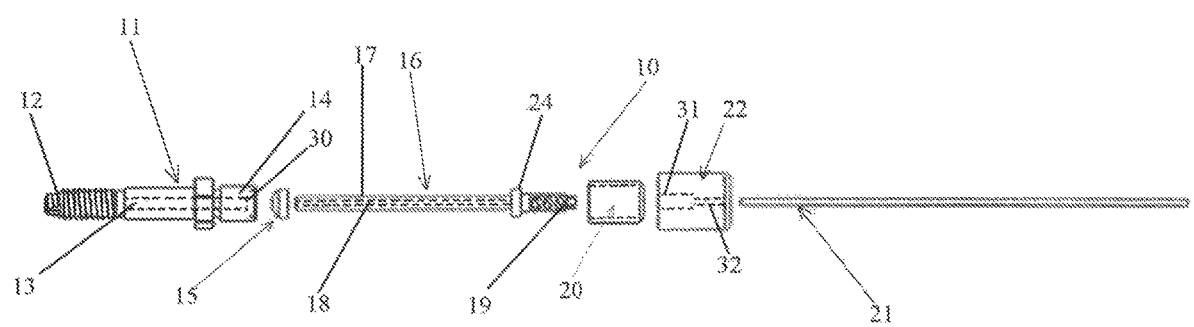
FIG. 1 is a lateral plan view showing an anchor bolt positioned to receive the reducing tube of the invention.
Figure 2:
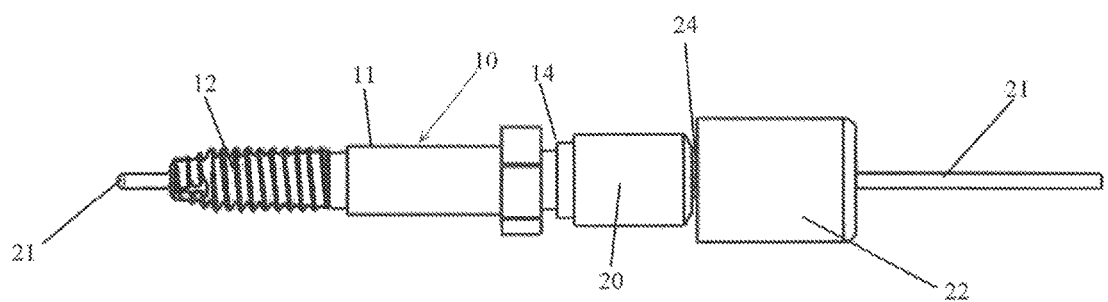
FIG. 2 is a lateral plan view showing the anchor bolt fixation system of FIG. 1 in the assembled state.
Figure 3:
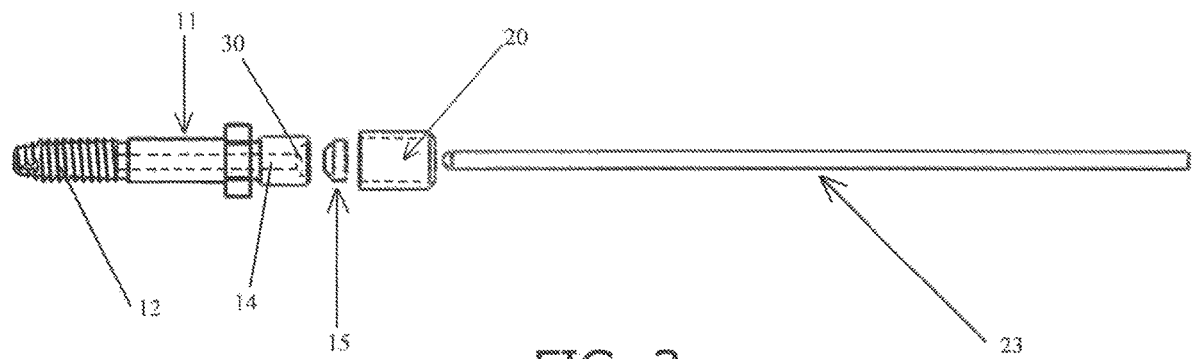
FIG. 3 is a lateral plan view showing the anchor bolt of FIG. 1 in an unassembled state for use without the reducing tube.
Figure 4:
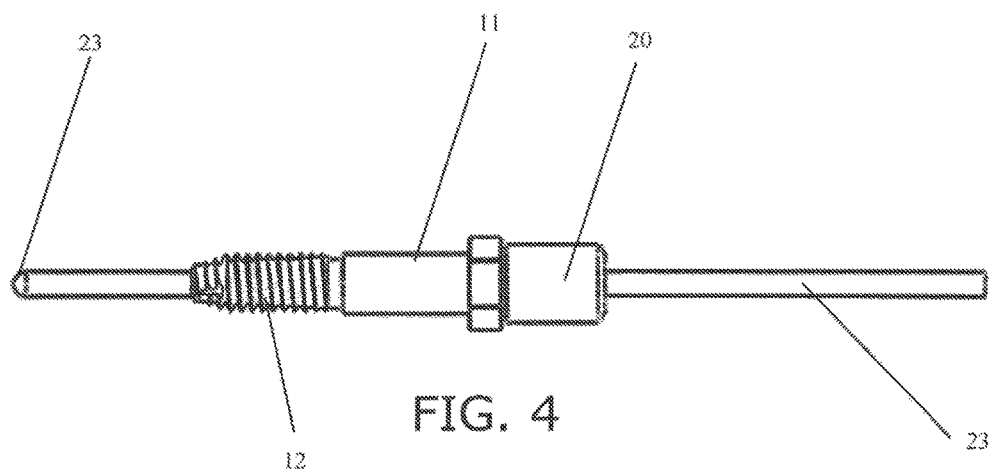
FIG. 4 is a lateral plan view showing the anchor bolt system of FIG. 3 in the assembled state.

Referring to FIGS. 1-5, FIGS. 1 and 2 show anchor bolt fixation system 10 utilizing anchor bolt 11 with reducing tube 16 to provide for a smaller diameter catheter, such as an sEEG depth electrode. In FIGS. 3 and 4 the anchor bolt fixation system 10 is shown utilizing the anchor bolt 11 with a larger diameter catheter, such as a laser ablation probe. FIGS. 5A-5E show the utilization of the anchor bolt fixation system 10 in connection with anchor bolt 11 positioned in the skull by means of the adjusted bushing 27 of a stereotactic frame 26.

Referring further to FIGS. 1 and 2, the anchor bolt 11 used in the anchor bolt fixation system 10 is shown to have a threaded end 12 which is threaded into a burr hole previously drilled into the skull of a patient. FIG. 1 shows the various elements of the anchor bolt system 10 in an aligned and separated state, whereas FIG. 2 shows the anchor bolt fixation system 10 in the assembled state.

In FIG. 1, the anchor bolt 11 is shown to have an axially disposed lumen 13 which extends from the threaded end 12 to the opposite end 14. Reducing tube 16 having an elongated body 17 with lumen 18 is shown having a threaded end 19. As further shown gasket 15 i.e. a medical grade silicone or like polymeric gasket, is shown aligned between the reducing tube 16 and anchor bolt cap 20 which fixes the reducing tube 16 to the anchor bolt 11 and anchor bolt cap 22 which holds the depth electrode or catheter 21.

For example, anchor bolt 11 may be fixed in a 2.7 mm or 3.2 mm burr hole wherein an sEEG depth electrode is utilized as shown in FIGS. 1 and 2. Additionally anchor bolt 11 may also be used in a procedure with a laser ablation probe as shown in FIGS. 3 and 4. The anchor bolts, lumen and probes of the invention may be used in conjunction with stereotactic frame equipment, for example, wherein an anchor bolt is targeted for positioning into the burr hole in a skull.

Referring further to FIG. 1, the anchor bolt 11 is constructed to accept both the reducing tube 16 and the larger diameter probe, such as a laser ablation probe 23. The silicone gasket 15 is shown for positioning in indentation 30 in the end 14 of the anchor bolt 11 to thereby seal the reducing tube 16 when positioned within the lumen 13 of the anchor bolt. The reducing tube 16 has a lumen 18 constructed to accept the smaller diameter catheter probe 21. The peripheral lip 24 of the reducing tube 16 abuts the silicone gasket 15 and the anchor bolt cap 20 is structured to threadingly engage end 14 of the anchor bolt 11 and fixes the reducing tube to the anchor bolt 11. Anchor bolt cap 22 is structured for threading onto the threaded end 19 of the reducing tube 16 for access to anchor bolt 11. The anchor bolt cap 22 is further shown to have a coaxial bore 32 having a smaller diameter for guiding the smaller diameter depth electrode or catheter 21. FIG. 2 shows the assembled anchor bolt fixation system 10 structured to be utilized with the smaller diameter catheter such as a sEEG depth electrode 21, shown fixated in the anchor bolt system.

Specifically, catheter 21 or the like has an approximate outside diameter which is constructed and arranged to slidingly fit through and within inside aperture or bore 32 of cap 22 and lumen 18 of reducing tube 16. Similarly, reducing tube 16 has an outside diameter which is constructed and arranged to slidingly fit through and within lumen 13 which extends through anchor bolt 11 having end 14. End 14 of anchor bolt 11 has an outside diameter which is constructed and arranged to threadingly engage the internal threads within cap 20. Threaded end 19 of reducing tube 16 is constructed to threadingly engage interior threads positioned on the inside of the bore 31 of anchor bolt cap 22 to thereby secure cap 22 to the end of the reducing tube 19 and to thereby provide access to the lumen 18 of the anchor bolt 11.

The cap 22 is constructed of a medical grade polymeric structure with an integral internal silicone gasket. Alternatively, the gasket may be positioned and constructed in cap 22 similar to that discussed above with respect to gasket 15 and anchor bolt cap 20.

The anchor bolt 11 may be formed of Grade 23 titanium or of a polymeric composition (i.e., a glass filled nylon) and having a lumen 13 with a diameter of approximately 1.8 mm so as to receive an ablation probe having a diameter of approximately 1.65 mm, for example. The latter providing clearance for the introduction and removal of the probe.

The reducing tube 16 may be constructed of titanium and have a length of approximately 20 mm and should not extend beyond distal end 12 of the anchor bolt 11. The anchor bolt cap 20 may be constructed of titanium (Grade 23) or of a polymeric composition, i.e., a glass filled nylon. The anchor bolt cap 22 may be constructed of a polymeric composition, but may also be constructed of titanium (Grade 23). The lumen 18 of the reducing tube 16 may be approximately 0.9 mm to receive an sEEG depth electrode having a diameter of approximately 0.8 mm, the difference for which providing clearance for the introduction and removal of the sEEG device.

Referring to FIG. 3, the anchor bolt 11 is shown constructed to accept both the reducing tube and larger diameter probe, such as a laser ablation probe. In the latter configuration, the silicone gasket 15 and anchor bolt cap 20 are utilized to fixate the larger diameter catheter 23 in the anchor bolt 11 without the use of the reducing tube. FIG. 4 shows the assembled anchor bolt fixation system structured to be utilized with the larger diameter catheter, such as a laser ablation probe.

Referring to FIGS. 5A-5E, a stereotactic frame 26 is shown having a bushing 27 directed at a specified point on the depiction of skull 28. The bushing 27 of the stereotactic frame 26 may be utilized to target and create a burr hole 25 in skull 28 and to threadingly position an anchor bolt 11 therein. The latter may be accomplished as disclosed in Applicant's Assignee's patent application entitled Anchor Bolt Driver Device having Ser. No. 15/171,221 filed on Jun. 2, 2016 and which is fully incorporated by reference herein.

Figure 5A:
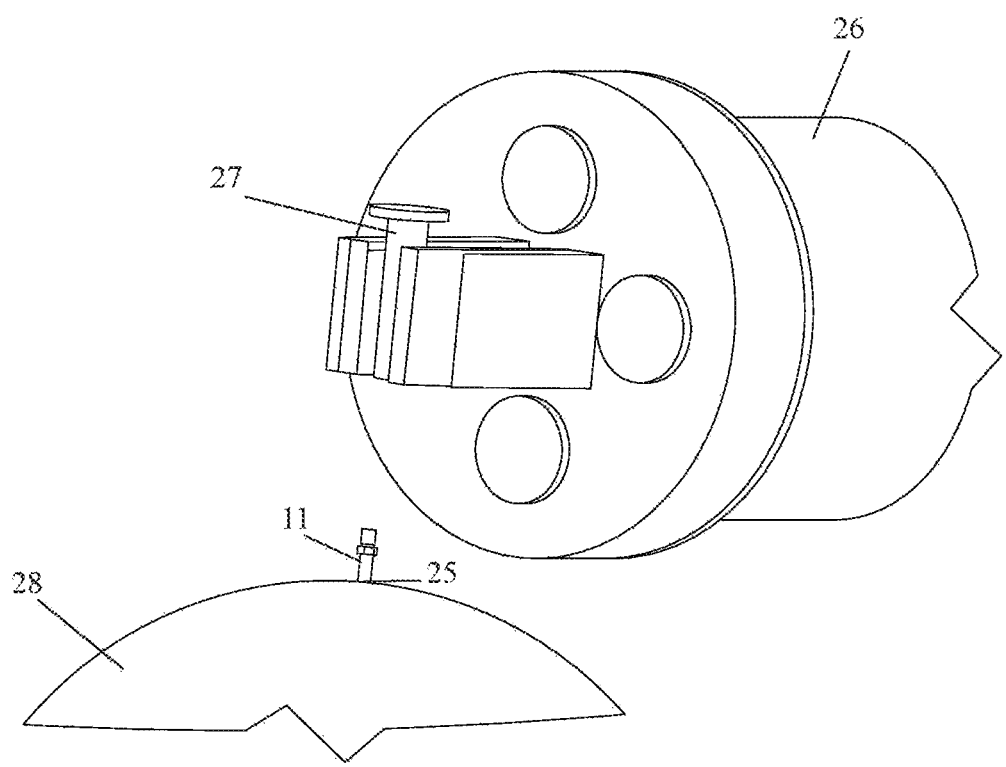
FIGS. 5A-5E are perspective views showing the anchor bolt fixation system of the present invention utilized in a stereotactic frame with an anchor bolt threaded into a burr hole in a skull as guided utilizing a stereotactic frame.
Figure 5B:
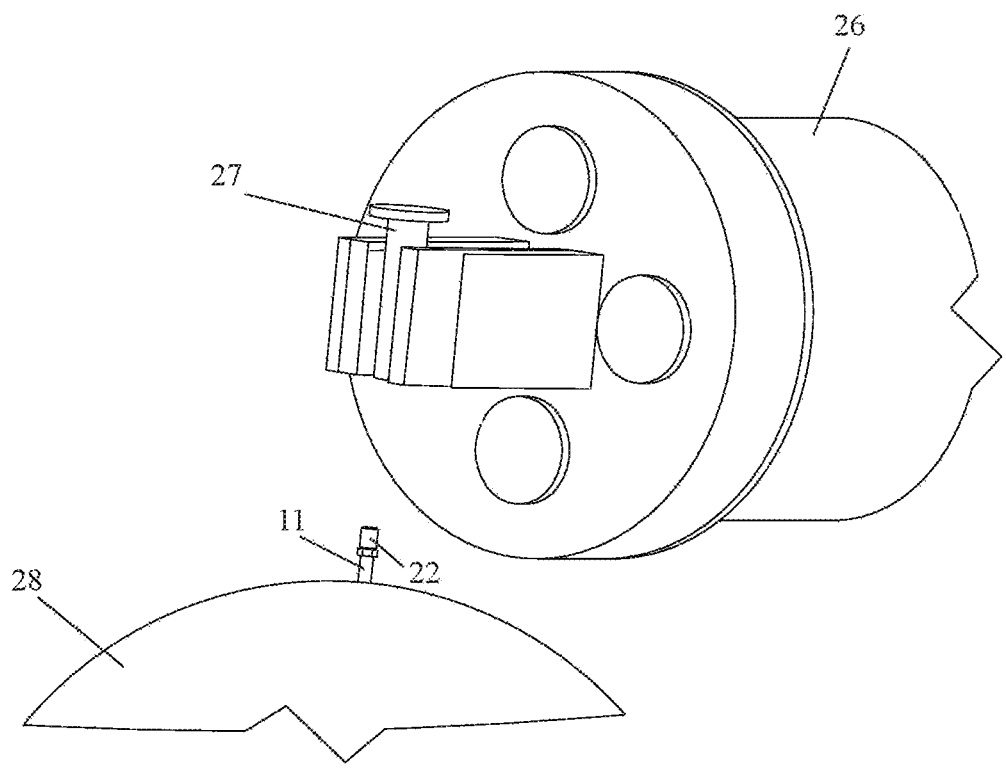
Figure 5C:
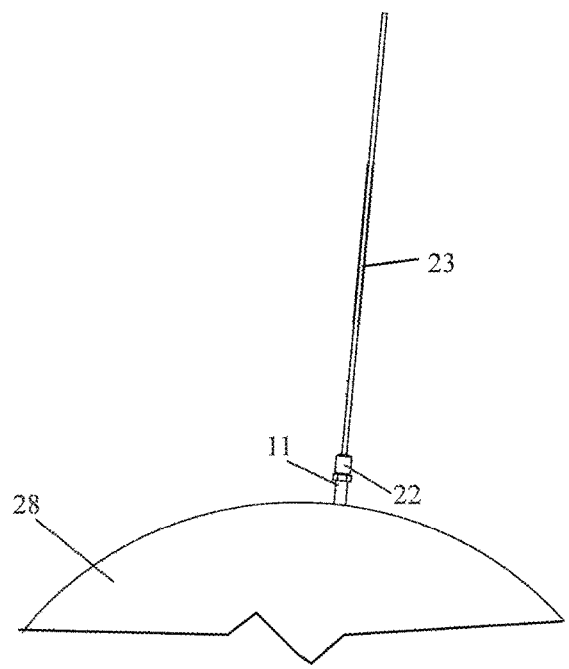

In FIG. 5B, anchor bolt 11 is shown having anchor bolt cap 22 threaded therein as shown in FIG. 4 to thereby allow the large diameter laser abrasion probe 23 to be manipulated through the lumen of the anchor bolt 11 and into the brain of a patient as shown in FIG. 5C.

Figure 5D:
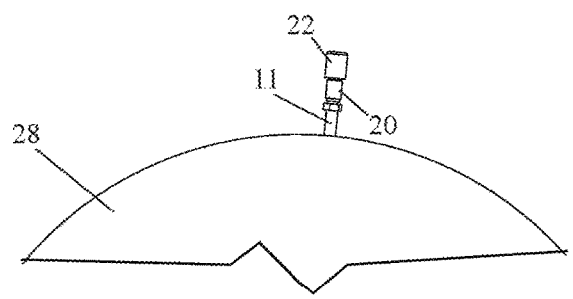
Figure 5E:
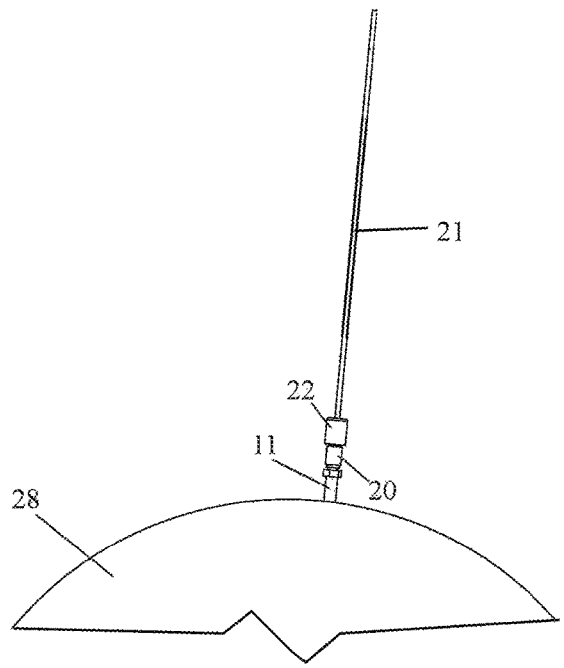

In FIG. 5D anchor bolt 11 is shown having anchor bolt cap 20 and anchor bolt cap 22 thereon as shown in FIG. 2 regarding the use of reducing tube 16 to thereby allow a smaller diameter depth electrode catheter 21 to be manipulated through the lumen of the anchor bolt 11 and into the brain of a patient as shown in FIG. 5E.

As many changes are possible to the anchor bolt fixation system embodiments of this invention utilizing the teachings thereof, the descriptions above, and the accompanying drawing should be interpreted in the illustrative and not in the limited sense.

That which is claimed is:

1. An anchor bolt fixation assembly having an anchor bolt with a lumen, a threaded end for engaging a burr hole in the skull of a patient, and an opposite indented end concentric the lumen, said assembly comprising
   a) a gasket for insertion into said indented end of said anchor bolt,
   b) a reducing tube having a lumen, a peripheral lip, and an externally threaded terminal end extending outward from said peripheral lip,
   c) a first anchor bolt cap for engaging said indented end of said anchor bolt, and
   d) a second anchor bolt cap having two coaxial bores, one said bore being adapted for the threaded engagement with said externally threaded terminal end extending from said peripheral lip of said reducing tube.

2. The anchor bolt fixation assembly of claim 1, wherein said lumen of said anchor bolt has a specified inside diameter and wherein said reducing tube has an exterior diameter generally equal said specified inside diameter of said anchor bolt.

3. The anchor bolt fixation assembly of claim 1, wherein said coaxial bores of said second anchor bolt cap comprises an internally threaded bore for attachment to said threaded terminal end of said reducing tube and a second bore having an inside diameter for receiving a catheter or depth electrode therethrough.

4. The anchor bolt fixation assembly of claim 1, wherein said assembly is utilized in connection with a stereotactic frame.

5. The anchor bolt fixation assembly of claim 1, wherein said gasket is formed of a medical grade silicone and wherein said first and second anchor bolt caps are formed of a titanium or a medical grade polymeric material.

6. The anchor bolt fixation assembly of claim 1, wherein said anchor bolt lumen has a diameter of approximately 1.8 mm to receive a laser ablation probe having a diameter of approximately 1.65 mm.

7. The anchor bolt fixation assembly of claim 1, wherein said lumen of said reducing tube has a diameter of approximately 0.9 mm to receive an sEEG depth electrode with a diameter of approximately 0.8 mm.

8. An anchor bolt fixation assembly comprising:
   a. an anchor bolt having a lumen, a first threaded end for engaging a burr hole in the skull of a patient and a second end having an indented cavity concentric said lumen;
   b. a gasket for positioning in said indented cavity of said second end of said anchor bolt;
   c. a first anchor bolt cap for the threading engagement with said second end of said anchor bolt;
   d. a reducing tube having an elongated cylindrical body with an outside diameter generally equal to said lumen of said anchor bolt, said reducing tube having a peripheral lip and an externally threaded terminal end extending outward therefrom, said reducing tube having a lumen with a second diameter; and
   e. a second anchor bolt cap having coaxial bores, with one said bore being adapted to secure said second anchor bolt cap to said externally threaded terminal end of said reducing tube, whereby the utilization of said first and second anchor bolt caps provide lumens with two distinct diameters for use with said anchor bolt.

9. The anchor bolt fixation system of claim 8, wherein said first anchor bolt cap second b has a bore with a diameter generally equal said second diameter of said lumen of said reducing tube.

10. The anchor bolt fixation system of claim 8, wherein said anchor bolt is positioned in the skull of a patient utilizing a stereotactic frame.

11. The anchor bolt fixation system of claim 10, wherein said anchor bolt is positioned in a burr hole of the skull of a patient through the lumen of a bushing of the stereotactic frame.

12. The anchor bolt fixation system of claim 8, wherein said gasket is comprised of silicone and wherein said first and second anchor bolt caps are comprised of a titanium or a medical grade polymeric material.

13. The anchor bolt fixation assembly of claim 8, wherein said lumen of said anchor bolt has a specified diameter and wherein said reducing tube is generally equal said specified diameter of said lumen of said anchor bolt.

14. The anchor bolt fixation assembly of claim 8, wherein said anchor bolt lumen has a diameter of approximately 1.8 mm to receive a laser ablation probe having a diameter of approximately 1.65 mm.

15. The anchor bolt fixation assembly of claim 8, wherein said second diameter of said lumen of said reducing tube is approximately 0.9 mm to receive an sEEG depth electrode with a diameter of approximately 0.8 mm.

\* \* \* \* \*